United States Patent [19]

Miyashita et al.

[11] Patent Number: 4,766,083

[45] Date of Patent: Aug. 23, 1988

[54] METHOD FOR THE PHOTOMETRIC DETERMINATION OF BIOLOGICAL AGGLUTINATION

[75] Inventors: Yoshinobu Miyashita; Haruki Oishi; Yasumichi Ueno; Hiromi Shiraishi, all of Osaka; Kazuyuki Tubaki, Hyogo, all of Japan

[73] Assignee: Wako Pure Chemical Industries, Ltd., Osaka, Japan

[21] Appl. No.: 481,961

[22] Filed: Apr. 4, 1983

[30] Foreign Application Priority Data

| Apr. 4, 1982 | [JP] | Japan | 57-55862 |
| Apr. 5, 1982 | [JP] | Japan | 57-56432 |
| Apr. 5, 1982 | [JP] | Japan | 57-56433 |
| Apr. 26, 1982 | [JP] | Japan | 57-70136 |

[51] Int. Cl.$^4$ ............ G01N 21/82; G01N 33/557
[52] U.S. Cl. ............ 436/517; 356/340; 356/342; 422/73; 436/34; 436/164; 436/805; 436/909
[58] Field of Search ............ 422/73; 436/517, 805, 436/164, 69, 909, 34; 356/341, 337, 338, 340, 342, 343

[56] References Cited

U.S. PATENT DOCUMENTS

| 3,420,609 | 1/1969 | Kozawa | 356/341 X |
| 4,043,669 | 8/1977 | Gehatia et al. | 356/341 X |
| 4,174,952 | 11/1979 | Cannell et al. | 422/73 X |
| 4,213,764 | 7/1980 | O'Connor | 436/805 X |
| 4,250,394 | 2/1981 | O'Connor | 436/805 X |
| 4,252,536 | 2/1981 | Kishimoto et al. | 422/73 X |
| 4,305,925 | 12/1981 | Kapmeyer et al. | 436/805 X |
| 4,313,929 | 2/1982 | Morita et al. | 436/805 X |
| 4,401,387 | 8/1983 | Tokinage et al. | 436/805 X |
| 4,597,944 | 7/1986 | Cottingham | 422/73 |

FOREIGN PATENT DOCUMENTS 0064230 9/1982 European Pat. Off. .
2377573 8/1978 France .
56-137140 10/1981 Japan .

OTHER PUBLICATIONS

Blume et al, Clin. Chem., vol. 21, No. 9, pp. 1234–1237, 1975.

Primary Examiner—Barry S. Richman
Assistant Examiner—Robert J. Hill, Jr.
Attorney, Agent, or Firm—Sughrue, Mion, Zinn, Macpeak, and Seas

[57] ABSTRACT

A photometric method and apparatus for measuring agglutination in a biological agglutination reaction system test sample using a laser beam source and at least one photodetector for detecting light scattered by the test sample. The method includes the following steps: (1) arranging the at least one photodetector so as to be capable of detecting scattered light from the test sample at a scatter angle of 30 to 60 with respect to a laser beam directed at the test sample from the laser beam source; (2) irradiating the test sample with the laser beam from the laser beam source; (3) selectively detecting the intensity of scattered light from the test sample at the scatter angle of 30 to 60 using the at least one photodetector which provides an output indicative thereof; and (4) determining the first derivative of the output of the at least one photodetector with respect to time and obtaining the maximum value thereof. In addition to the laser beam source and the at least one photodetector, the apparatus also includes a reaction cuvette for containing the test sample.

10 Claims, 5 Drawing Sheets

METHOD FOR THE PHOTOMETRIC DETERMINATION OF BIOLOGICAL AGGLUTINATION

BACKGROUND OF THE INVENTION

The present invention relates to a method and apparatus for the photometric determination of biological agglutination using light scattering. More particularly, the present invention relates to a method and apparatus for the photometric determination of biological agglutination of test samples by detecting scattered light through the test samples using a laser beam source and at least one photodetector.

The importance of determining biological agglutination systems such as antigens, antibodies, blood clotting, etc. with precision has long been recognized in various fields of life sciences as well as in the field of the therapy, and there has been stronger desire for the development of quantitative determination of antigens, antibodies, blood clotting, etc. with high precision as demand therefor has increased in recent years.

Determination heretofore prevailing which is a plate immune diffusion takes one or a few days and the judgement of the results obtained by this method is very complicated and requires skill. From this it follows that the judgement varies from person to person. This is one of the major defects of the conventional method.

Recently, there has been proposed a nephelometric immunoassay in order to detect the formation of antigen-antibody complexes with light scattering, thus improving operability and precision in quantitative determination. However, the conventional nephelometric immunoassay practically takes a relatively long time ranging from several tens of minutes to several hours and therefore is unsatisfactory when urgent detection or high speed treatment of a large amount of test samples is needed.

Further, it has heretofore been known to detect antigens or antibodies by reacting latex particles on which an antigen or an antibody is supported with a corresponding antibody or antigen on a glass plate and observing visually the state of agglutination which occurs. This method is disadvantageous since it gives only qualitative data by judging whether or not agglutination occurs on the glass plate and the judgement as to whether or not agglutination occurred will be apt to vary depending on personal conditions of those who carry out the detection in the borderline regions. A further disadvantage is that with the above method it is necessary to prepare a series of seriously diluted samples and judgement must be made on each diluted sample, which not only requires a lot of time and effort but also gives rise to semiquantitative data only, thus achieving but low precision.

On the other hand, it has been known to measure optical absorbance of a test sample in a reactor with a light whose wavelength falls in the near-infrared region in order to qualitatively determine the agglutination state. This method is disadvantageous in that on one hand, most of the transmission light to be detected is blank information which is ascribable to reduction by latex particles in a non-agglutinated state, and the change in the transmission light ascribable to the minor part of the latex particles which agglutinated is very small as compared with the blank value, and on the other hand, when measuring transmission, light sensitivity is lowered further because of multiple scattering in the light path since test samples has a very high turbidity and also it tends to be influenced by movement of the particles in the light path.

In the case where scattered light is utilized, a conventional method using an integrating-sphere photometer is also disadvantageous since the background value is large relative to the value due to agglutination as in the case of measuring the optical absorbance, resulting in decreases in sensitivity and stability.

As stated above, the conventional methods for measuring agglutination reactions are not satisfactory with respect to their precision since they are difficult to carry out in a stable manner with high sensitivity.

On the other hand, blood coagulation tests are extremely important and useful for successful therapy of a bleeding disorder in the patient or for the followup manangement of patients receiving therapy using an anticoagulant. Also, these tests must be done before an operation can be initiated.

The coagulation tests include measurements of prothrombin time hereafter referred to as "PT" and of activated partial thromboplastin time hereafter referred to as "APTT" which are well known and effected as measurements of an extrinsic blood clotting mechanism and intrinsic blood clotting mechanism, respectively.

Further, at present various automatic clottage detection devices capable of measuring PT and APTT are available commercially.

The process of blood coagulation is said to be an extremely complex chain reaction and involves blood coagulation factors I to XIII. It is therefore necessary to carry out quantitative determination of blood factors to see which factors are short and to what extent they are short in the case where disorder in PT or APTT is found.

For determining blood factors, a method has heretofore been used in which corrective reagents is used in PT or APTT tests to qualitatively detect which factor is insufficient and then a calibration curve should be obtained by the PT or APTT test using an appropriate blood factor-lacking plasma. This conventional method requires very complicated procedures and much work. In addition, the quantitative determination of the results is not so accurate since the determination method is indirect in nature.

In contrast to tests based on the gross blood coagulation, direct determination of each blood factor has recently been proposed which involves measurement of immune activity using an antigen-antibody reaction of measurement of biological activities using an enzymatic reaction with a synthetic substrate.

According to this method direct measurement can be carried out with ease and high specificity and precision. However, conventional apparatus for the measurement of PT or APTT cannot be used for this method and it is therefore necessary to provide therewith new costly devices so that the apparatus can be adapted to the direct measurement method described above.

On the contrary, conventional apparatus adapted for the direct determination of blood factors by the above method cannot be used for carrying out screening tests which are very useful in blood coagulating tests such as PT, APTT, etc.

SUMMARY OF THE INVENTION

As a result of extensive research it has been found that in a nephelometric immunoassay using a laser beam as a light source, there is a selective range of detection angle at which the intensity of scattered light due to antigen-antibody complex changes very sharply in the initial stage of the reaction where antigen-antibody complex is formed in the fluid sample. The present invention is based on the above findings.

Therefore, the present invention provides a photometric method for measuring a biological agglutination reaction comprising irradiating a biological agglutination reaction system with a laser beam and selectively detecting the intensity of scattered light from the reaction system at a scattering angle ($\theta$) of 30° to 60°.

Further, the present invention provides a photometric apparatus for measuring a biological agglutination reaction system comprising a laser beam source and at least one photodetector for detecting scattered light from a test sample, the method comprising arranging a photodetector so as to be capable of detecting the scattered light at a scatter angle ($\theta$) of 30° to 60°.

According to the present invention biological agglutination reactions can be measured quantitatively by simple operations. Further, antigen-antibody reactions can be measured in a very short time with high precision as compared with conventional nephelometric immunoassays.

Further, according to the present invention immunological agglutination reactions can be determined quantitatively with high stability and precision.

Still further, according to the prsent invention, determination of blood coagulation such as conventional PT and APTT tests and immunological determination of blood factors using antigen-antibody reactions can be carried out efficiently in a single device, which makes it possible to conduct screening tests and quantitative determination tests with ease and high precision.

BRIEF DESCRIPTION OF THE DRAWINGS

The present invention will be described in detail with reference to the drawings in which:

FIG. 2 (b) is a graph showing time differential characteristics of the curve A in FIG. 2 (a);

DETAILED DESCRIPTION OF THE INVENTION

Examples of suitable laser beams include a helium neon laser having an oscillation wavelength of 632.8 nm or visible - near-infrared semiconductor laser having an oscillation wavelength of 700–800 nm.

In the present invention, there can be used insoluble carrier particles of organic high molecular substances which are insoluble in a liquid medium used in the measurement and have an average particle size of not larger than 0.1 micron, such as latex of organic polymer e.g., polystyrene, styrene-butadiene copolymer, etc. obtained by emulsion polymerization, or inorganic oxides such as silica, alumina, etc.

Figure 1:
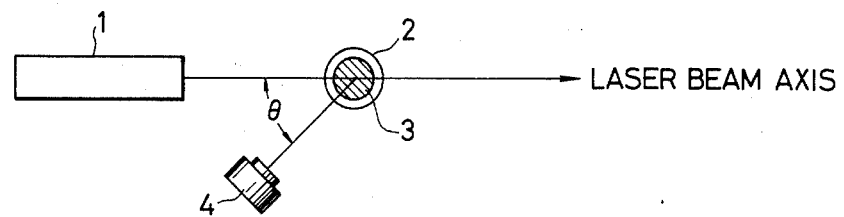
FIG. 1 is a schematical illustration of the principle of the photometric system of the present invention.

FIG. 1 shows the arrangement of a laser beam source, a test fluid sample which is a scattered light source, and a photodetector according to one embodiment of the present invention. A predetermined amount of laser beam flux emitted from a laser beam source 1 is irradiated to a cuvette 2, which contains a test fluid sample 3, and the sample scatters the laser beam.

A photodetector 4 for measuring the intensity of the scattered light and converting it into an electric signal is provided at a specific position with respect to the reaction cuvette 2. The laser beam source 1 may be a visible semiconductor laser having an oscillation wavelength of about 780 nm. The reaction cuvette 2 may be a test tube cuvette having an inner diameter of 5 mm, for example. The photodetector 3 may be a silicon photocell.

Assuming the angle of the photodetector 4 with respect to the laser beam axis passing the center of the reaction cuvette 2 is $\theta$, time response of the intensity of scattered light according to the formation of antigen-antibody complex differs depending on the angle at which scattered light is detected.

Figure 2A:
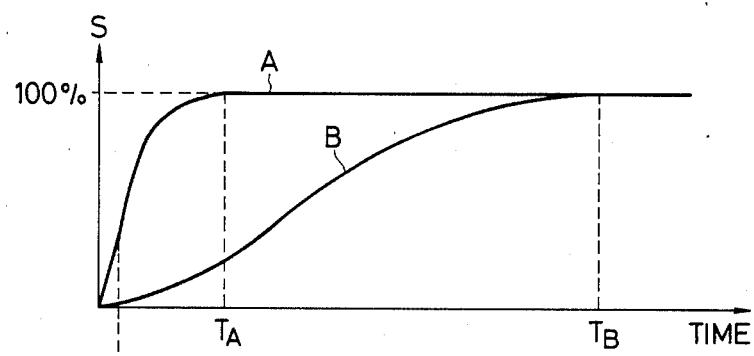
FIG. 2 (a) is a graph plotting against time the intensity of scattered light from a fluid sample.
Figure 2B:
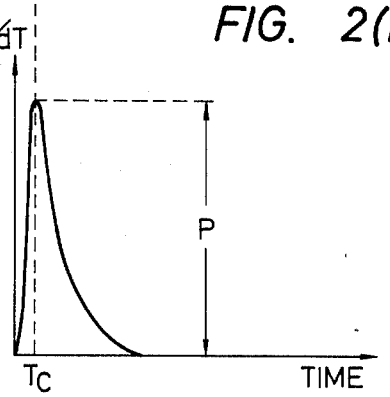

In FIG. 2 (a), A is a curve plotting against time the change in the intensity of scattered light (S) as the reaction between an antigen and a corresponding antibody to form a complex proceeds as measured at a scatter light angle ($\theta$) of 50° in the above described apparatus.

The moment when a solution containing an antigen or antibody to be determined is mixed with a reagent containing a corresponding antibody or antigen the intensity of scattered light (S) begins to increase and reaches a stationary level after time $T_A$ and this level is maintained thereafter.

In so-called "end point" method, the height of this final level after time $T_A$ is used for quantitative determination of antigens and antibodies.

Therefore, the shorter the time required in which the final level is reached, i.e., the higher the speed at which the intensity of scattered light (S) increases, the more rapidly can the determination be carried out.

In conventional nephelometric immunoassays forward scattered light (scatter angle $\theta$ is not smaller than 90°) is used.

In FIG. 2 (a), the curve B is a plot against time of the intensity of scattered light measured at a scatter angle ($\theta$) of 150°. In FIG. 2 (a), the vertical axis is normalized taking the amount of light finally reached as 100 in order to enable one to compare the results obtained by measuring at a scatter angle of 50°.

It has been found when $\theta$ is 150°, the time $T_B$ required for reaching a stationary level is several fold longer than the corresponding time $T_A$ which is obtained when $\theta$ is 50°. Practically, $T_A$ is on the order of a few minutes in contrast to $T_B$ which is on the order of several tens of minutes. This supports the view that the sensitivity of detection in the initial stage of the formation of an antigen-antibody complex is higher in the measurement of backward scattered light than in the measurement of forward scattered light, and that this difference is ascribable to the difference in spatial distribution of the intensity of scattered light due to the size of the antigen-antibody complex.

In conventional nephelometric immunoassays the measurement of forward scattered light is generally used aiming at obtaining higher intensity of scattered light. On the contrary, fixing their eye on the sensitivity of detection in the initial stage of antigen-antibody reaction the present inventors have found that backward scattered light reflects the state of the reaction in its initial stage very sensitively.

It has also been found that at a scatter angle of smaller than 30° the signal of scattered light itself is weak and the influence of a reflected light reflected by the reactor is strong, thus the precision of determination being reduced.

Further, it has been found according to the present invention that a scatter angle range of from 30° to 60° is most sensitive to the leading edge of the antigen-antibody reaction and enables one to carry out photometric determination with high precision. If photometric detection is done at a scatter angle in this range, signals of a level sufficient for further processing in a conventional electric circuit can be obtained.

Therefore, photometric measurement with high precision can be carried out in a time ($T_A$) by several tenths shorter than time $T_B$ required for the measurement according to conventional nephelometric immunoassays.

FIG. 2 (b) is a graph plotting a first time differential (dS/dT) of A in FIG. 2 (a) which is a curve showing time response of the intensity of scattered light according to the present invention.

In the dynamic nephelometric immunoassay, the maximum value (P) of the above first time-differential signal is used in the quantitative determination of antigen or antibody.

Time required for the measurement is Time $T_C$, which is the time from the initiation of reaction to the appearance of P, and it is observed that $T_C$ is shorter than $T_A$. This means that the time required for measurement is further shortened than required for the end point method.

Figure 3:
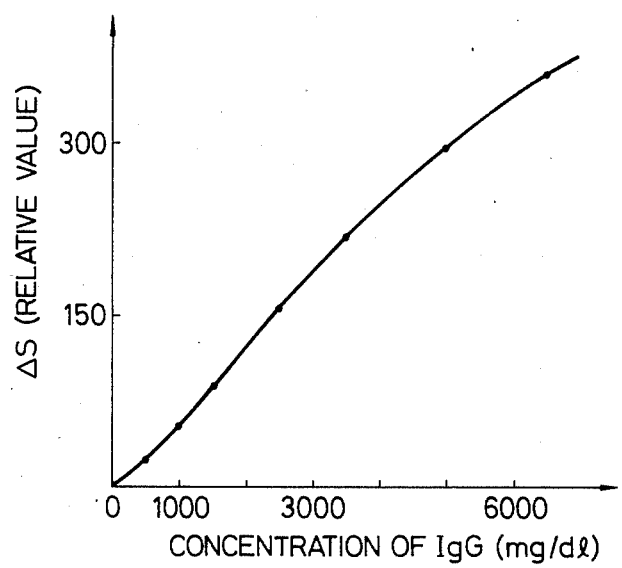
FIG. 3 is a graph showing a calibration curve plotting the concentration of an antigen versus the intensity of scattered light in the determination of IgG.

FIG. 3 shows a calibration curve for human immunoglobulin G (IgG) obtained by using the above described apparatus.

In this embodiment, 30 microliters each of 301 fold diluted solutions of standard serum containing various concentrations of human IgG were added to 300 microliters of a 12.5 fold diluted solution of anti-IgG serum (sheep), and the mixture was incubated for 5 minutes at room temperature. Then, the output of the photodetector was read and the relationship between the difference in the intensity $\Delta S$ (i.e., the intensity of scattered light after 5 minutes from the initiation of the reaction minus that of scattered light before the reaction took place) and concentration was obtained.

In 5 minutes calibration relation sufficient for the quantitative determination was obtained. In contrast it takes about 30 minutes to about 1 hour for a like determination according to conventional end point method. Thus, the photometric system of the present invention is more efficient than the prior art.

More speedy measurement can be achieved using a method in which the concentration of an antigen or antibody can be determined from the speed of change in the intensity of scattered light (i.e., dynamic nephelometric immunoassay).

Figure 4:
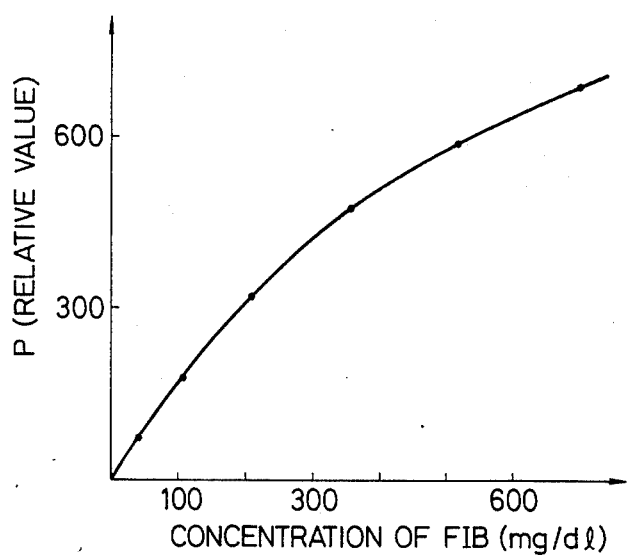
FIG. 4 is a graph showing a calibration curve plotting the concentration of an antigen versus maximum speed (peak rate) of the change in the intensity of scattered light.

FIG. 4 shows a calibration curve for the determination of fibrinogen in blood serum (hereafter referred to as "FIB") obtained by a dynamic nephelometric immunoassay using P by the use of the above described apparatus.

More particularly, 50 microliters of a 21 fold diluted solution of standard plasma containing an FIB antigen at different concentrations was added to 300 microliters of a 12.5 fold diluted solution of an anti-FIB serum (rabbit), and the mixture was detected by the above described apparatus. The output of the photodetector was processed by a conventional differential electric circuit and the relationship between the maximum value P of the first time-differential and the concentration of the sample was obtained.

In the dynamic nephelometric immunoassay, high detection sensitivity is needed in the initial stage of the reaction. The present invention is advantageous in this respect since it permits highly sensitive detection immediately after the initiation of the reaction.

Figure 5:
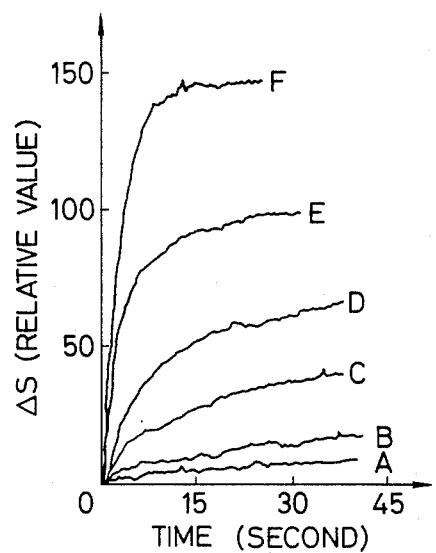
FIG. 5 is a graph plotting against time the change in the intensity of scattered light obtained by irradiating reaction mixtures composed of standard FIB solutions at various concentrations and anti-FIB solutions at various concentrations and anti-FIB-sensitized latex with a laser beam having a wavelength of 780 nm.

FIG. 5 shows a time response of the intensity of scattered light accompanying an agglutination reaction at its initial stage when it is carried out using polystyrene latex having an average particle size of 0.08 microns and detection was carried out at a scatter angle ($\theta$) of 50° using the above described apparatus of the present invention.

The polystyrene latex used is a product of Dow Chemical Inc. and sensitized with human fibrinogen (FIB) antibody (rabbit) by the method described in *Journal of Laboratory and Chemical Medicine* 50 pp 113–118.

Output S of the photodetector of the above apparatus was recorded from the point in time when 50 microliters of standard plasma containing different concentrations of FIB antigen was added to 300 microliters of the sensitized latex.

In FIG. 5, the vertical axis $\Delta S$ indicates that the observed values are adjusted by deducing therefrom the ouput $S_0$ of the photodetector at the moment when the latex solution and the FIB antigen solution were mixed with each other, as a blank value.

In the Figure, curves A, B, C, D, E and F correspond to the concentrations of the FIB: 0.0298, 0.0595, 0.119, 0.238, 0.476 and 0.952 mg/dl, respectively.

According to the present invention, as will be clear from the figure, it is possible to detect the change in the intensity of scattered light due to the agglutination which occurs in an extremely turbid test fluid sample, in a very stable state and with high sensitivity.

Figure 6:
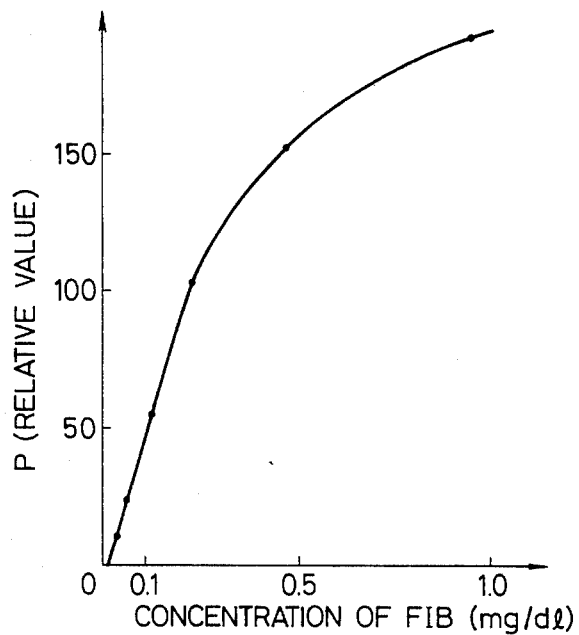
FIG. 6 is a graph showing a calibration curve plotting the maximum speed of the change in the intensity of scattered light versus the concentration of a standard FIB solution.

FIG. 6 shows a calibration curve prepared from the maximum speed of the time response of agglutination signal $\Delta S$ shown in FIG. 5. That is, the signal $\Delta S$ obtained by correcting the output (S) of the photodetector with the blank value was processed by a conventional differential electric circuit and the relationship between the maximum differential value $P = (d(\Delta S)/dT)_{Max}$ and the concentration of FIB was obtained. The time required for the measurement of one sample was 15 seconds only.

The present invention thus provides a photometric method and system which are very sensitive in the detection of the initial stage of an agglutination reaction and permit rapid measurement.

Figure 7:
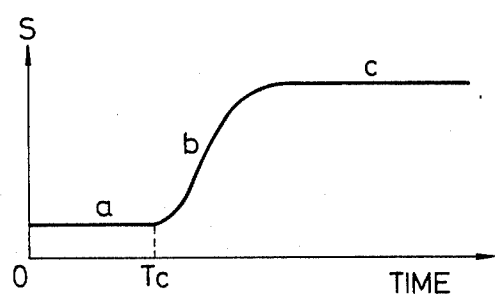
FIG. 7 is a graph plotting the intensity of scattered light versus time of a test fluid sample of a blood coagulation reaction.

Further, blood coagulation can be measured using the photodetector 4 in FIG. 1. FIG. 7 is a graph showing a time response of the intensity of scattered light (S) in the reaction of blood coagulation using the photodetector 4.

In FIG. 7, which is a graph showing a time response of the intensity of scattered light (S) in the reaction of blood coagulation, portion a represents a state in which the coagulation reaction proceeds after mixing a test sample with a reagent but precipitation of fibrin is not observed, portion b represents a state in which precipitation of fibrin proceeds vigorously, portion c represents a state conversion of fibrinogen (FIB) into fibrin and precipitation of fibrin was completed. It is empirically known that the point in time $T_c$ at which the switch over from a to b occurs corresponds to the initiation of the precipitation of fibrin.

Figure 8:
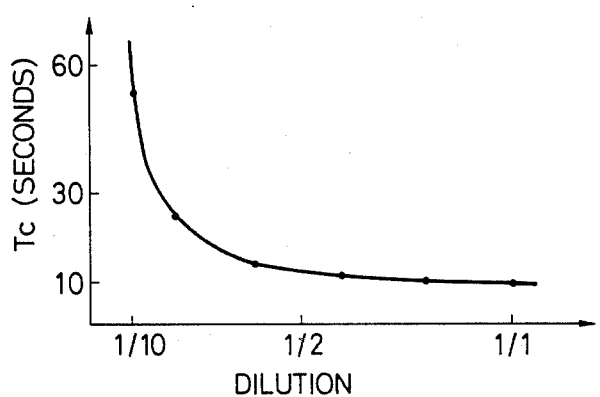
FIG. 8 is a graph showing an activity curve obtained in the measurement of PT.

FIG. 8 shows the relationship of the degree of dilution of human plasma from a sound person with physiological saline and $T_c$ in the PT measurement (hereafter referred to as "activity curve" obtained by the use of the device described above.

More particularly, 100 microliters of a citric acid-added normal human plasma diluted with physiological saline, 100 microliters of thromboplastin preparation (derived from rabbit brain) and 100 microliters of an aqueous solution of 0.02 M calcium chloride were mixed and the change in the intensity of scattered light from the resulting mixture was observed. From the results $T_c$ was obtained and the relation between the degree of dilution of the normal human plasma preparation and $T_c$ were plotted.

According to the present invention, stable activity curves were obtained even when samples having coagulation activity as low as 10 fold dilution were used.

Although it is known to obtain $T_c$ from the change in the intensity of scattered light accompanying the blood coagulation reaction it is unexpected that the measurement of blood coagulation can be carried out with high sensitivity and stability even when low activity coagulation reactions are measured if a laser beam having a high intensity and excellent monochromaticity is used.

According to the above embodiment of the present invention, the measurement of a coagulation reaction and that of an antigen-antibody reaction can be carried out using the same photodetector, so that the photometric system can be simplified.

Figure 9:
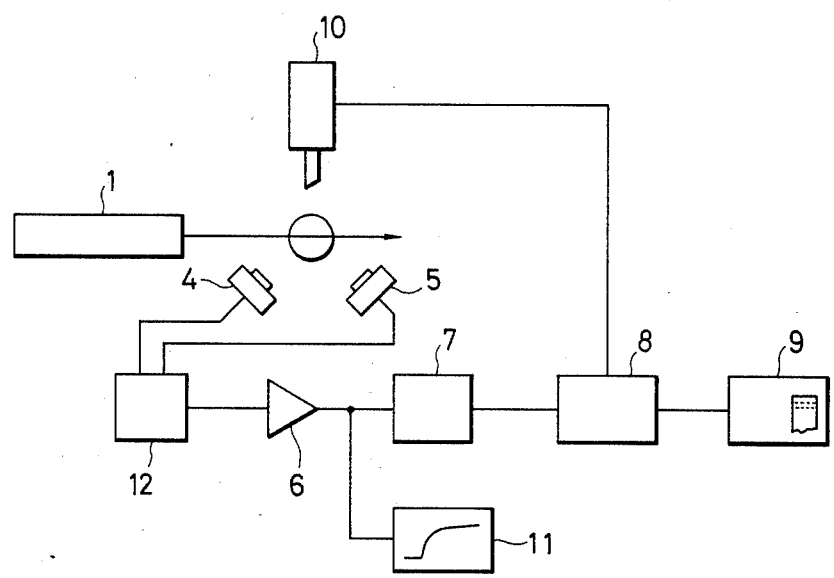
FIG. 9 is a block diagram of a photometric apparatus for measuring the intensity of scattered light according to one embodiment of the present invention.

FIG. 9 is a block diagram of the apparatus for the determination of scattered light which comprises two photodetectors.

In FIG. 9, photodetectors 4 and 5 convert the intensity signal of scattered light into an electric signal, which is then input to a signal preconditioner 6 and processed thereby. A signal switch 12 determines which of the signals from the photodetectors 4 and 5 is to be input to a signal preconditioner 6 and processed therein. The signal preconditioner 6 further differentiates the results when the measurement of the antigen-antibody reaction utilizing P is carried out using electrical amplification and the results obtained are input to an A/D converter 7. A computer 8 is provided so that it can evaluate the information in the form of the intensity of scattered light converted into digital amount by the A/D convertor, judge the point of coagulation when blood coagulation is measured and calculate the concentration of antigens or antibodies when an antigen-antibody reaction is measured.

It is obvious to one skilled in the art that in addition to the above described embodiments various procedures can be used and various programs therefor can be formulated as methods for judging the point of blood coagulation, and for calculating the concentration of antigens or antibodies. These modifications are not understood to limit the present invention in anyway.

Further, a display and print portion 9 is provided for displaying and printing the data processed by the computer 8. Also, a recorder 11 is provided so as to continuously observe the process of the reaction. Further, the system comprises a reagent dispensing means and sample preparation means 10.

As stated above, a combination of the present invention and conventional techniques will bring about automated, energy conservated measurement of scattered light and apparatus therefor with ease.

Further, the present invention can determine the change in the intensity of scattered light from biological agglutination systems such as an immunological agglutination reaction system very stably and with high sensitivity and quantitative reproducibility and therefore, data with high precision can be obtained rapidly.

Further, the present invention enables one to determine blood coagulation and antigen-antibody reactions, which have been unable to be determined by a single apparatus of conventional techniques, with high precision, and therefore it contributes greatly to efficient and rationalized measurement. Further, according to the present invention, detailed clinical data can be obtained before clinical tests can be conducted, thus adding to the field of therapy greatly.

What is claimed is:

1. A photometric method for detecting agglutination in a biological agglutination reaction system test sample using a photometric apparatus comprising a laser beam source and at least one photodetector for detecting light scattered by the test sample, the method comprising:
    (1) arranging said at least one photodetector so as to be capable of detecting scattered light from the test sample only at a scatter angle of 30° to 60° with respect to a laser beam directed at the test sample from the laser beam source;
    (2) irradiating the test sample with the laser beam from the laser beam source;
    (3) selectively detecting the intensity of scattered light from the test sample at the scatter angle of 30° to 60° using the at least one photodector which provides an output indicative thereof; and
    (4) determining the first derivative of the output of said at least one photodetector with respect to time and obtaining the maximum value thereof.

2. The photometric method as claimed in claim 1, wherein said laser beam has a wavelength of below 800 nm.

3. The photometric method as claimed in claim 1, wherein said laser beam source is a helium-neon laser having an oscillation wavelength of 632.8 nm.

4. The photometric method as claimed in claim 1, wherein said biological agglutination reaction system test sample is a mixture of an antigen or antibody to be determined and a coresponding antibody or antigen.

5. The photometric method as claimed in claim 4, wherein said laser beam source is a semiconductor laser having an oscillation wavelength of 780 nm.

6. The photometric method as claimed in claim 4, wherein said antigen to be determined is human fibrinogen and said corresponding antibody is an antibody to human fibrinogen.

7. The photometric method as claimed in claim 4, wherein said biological agglutination reaction system test sample comprises a mixture of a solution of said antigen or antibody to be determined and insoluble carrier particles having a mean particle size of below 0.1 micron having immobilized thereon said antibody or antigen corresponding to said antigen or antibody to be determined.

8. The photometric method as claimed in claim 7, wherein said insoluble carrier particles are made of a latex of an organic polymer or are made of an inorganic oxide.

9. The photometric method as claimed in claim 8, wherein said organic polymer is polystyrene or a styrene-butadiene copolymer.

10. The photometric method as claimed in claim 8, wherein said inorganic oxide is silica or alumina.

* * * * *